United States Patent [19]

Giordano et al.

[11] Patent Number: 5,157,156
[45] Date of Patent: Oct. 20, 1992

[54] PROCESS FOR PREPARING AN INTERMEDIATE USEFUL IN THE SYNTHEIS OF PROBUCOL

[75] Inventors: Claudio Giordano, Monza; Giuseppe Barreca, Milan, both of Italy

[73] Assignee: Zambon Group S.p.A., Vicenza, Italy

[21] Appl. No.: 733,114

[22] Filed: Jul. 19, 1991

[30] Foreign Application Priority Data

Jul. 26, 1990 [IT] Italy .................. 21071A/90

[51] Int. Cl.$^5$ ........................... C07C 319/02
[52] U.S. Cl. ....................... 568/64; 562/74; 562/833
[58] Field of Search ............. 568/64; 562/74, 833

[56] References Cited

U.S. PATENT DOCUMENTS 3,673,247  6/1972  Hill. Jr. et al. ............ 562/833
4,056,568  11/1977  Cisneg ........................ 568/64
4,625,000  11/1986  Chao et al. .................. 525/534

FOREIGN PATENT DOCUMENTS 0190685  8/1986  European Pat. Off.
0275952  7/1988  European Pat. Off.

OTHER PUBLICATIONS

Tetrahedron Letters, vol. 21, pp. 1235–1238, Pergamon Press GB 1980, "Direct Reduction of Sulfonic Acid to the ..."(Numata).
Tetrahedron Letters, vol. 21, pp. 4921–2924, Pergamon ... UK, (1980) "Iodine Catalyzed reduction of Arenesulfonic ... " (Fujimori).
Bull. Chem. Soc. Jpn. 56, 3802–3812 (1983) vol. 56, No. 12 "Reduction of Sulfonic Acids and Related Organosulfur ... " (OAE).
Voronkov, M. G. et al., "Synthesis", (1982) p. 277–280.

Primary Examiner—Marianne M. Cintins
Assistant Examiner—John Peabody
Attorney, Agent, or Firm—Stevens, Davis, Miller & Mosher

[57] ABSTRACT

A process for preparing 2,6-di-t-butyl-4-mercapto-phenol. This is accomplished by sulfonation of the phenol with a silylated sulfonating agent (e.g., trimethylsilyl-chlorosulfonate). The sulfonic acid is then reduced directly or is converted to the sulfonyl halide intermediate which is then reduced to yield the 2,6-di-t-butyl-4-mercapto-phenol.

7 Claims, No Drawings

PROCESS FOR PREPARING AN INTERMEDIATE USEFUL IN THE SYNTHEIS OF PROBUCOL

The present invention relates to an improvement in the process for preparing 2,6-di-t-butyl-4-mercapto-phenol, useful as intermediates in the synthesis of a number of drugs.

Probucol, i.e. 4,4'-(isopropylidenedithio)-bis-[2,6-di-t-butylphenol] (Merck Index, XI, Ed., No. 7761, page 1230), is a known during having hypolipemic activity which has been described for the first time in the British Patent No. 1199871 in the name of Consolidation Coal Company.

The above-mentioned British patent also discloses a method for preparing probucol by condensing 2,6-di-t-butyl-4-mercapto-phenol with acetone.

Afterwards, many methods for preparing 2,6-di-t-butyl-4-mercapto-phenol were disclosed.

The known methods comprise functionalizing the 4-position of 2,6-di-butyl-phenol with a group convertible into a mercapto group, preferably by reduction.

Several approaches have been studied in order to enter a suitable precursor group into the 4-position of the phenol-derivative.

Among them the most common ones are the introduction of the thiocyanate function and the sulfonation reaction.

An example of the first approach is disclosed in U.S. Pat. No. 3,129,262 (Consolidation Coal Company) wherein 2,6-di-t-butyl-phenol is treated with thiocyanate and bromine to afford the corresponding 4-thiocyanate-phenol which then gives the desired 4-mercapto-phenol via reduction with sodium and ammonia.

While showing good selectivity in the functionalization step, this method has the serious drawback of releasing hydrogen cyanide during the reduction step. Of course, the extreme dangerousness of hydrogen cyanide gives rises to serious problems on industrial scale.

In turn, as far as the sulfonation reaction is concerned, it is known that sulfonation of t-butylphenols gives large quantities of by-products because of concurrent isomerization and dealkylation reactions (Lambrechts et al., J. Chem. Soc., Perkin Trans II, 1985, pages 677–682).

Even in the process of the Spanish Patent No. 485474 (Istituto de Investigacion y Desarollo Quimico y Biologico S.A.), notwithstanding that the sulfonation reaction is performed on a derivation of 2,6-di-t-butyl-phenol having the phenolic function suitably protected as acetoxy, the desired sulfonated product is however obtained in low yield.

As a matter of fact, when the sulfonation reaction is carried out as described in the above-mentioned spanish patent, the amount of resulting by-products is large and anyhow greater than that of the desired product.

In addition, it is self-evident that the need of protecting the starting compound implies an increase in the overall cost of the process.

We have now surprisingly found an improved process for preparing the 2,6-di-t-butyl-4-mercapto-phenol via sulfonation of 2,6-di-t-butyl-phenol and subsequent reduction of the sulfonic group which has no need of protecting the functional groups and allows obtaining the desired product in almost quantitative yields.

It is therefore an object of this invention to provide an improved process for preparing the 2,6-di-t-butyl-4-mercapto-phenol comprising (i) the sulfonation of 2,6-di-t-butyl-phenol, (ii) the optional preparation of an easily reducible derivative of the thus obtained 2,6-di-t-butyl-4-hydroxybenzenesulfonic acid, and the reduction of the 2,6-di-t-butyl-4-hydroxybenzene-sulfonic acid or of an easily reducible derivative thereof, the improvement comprising carrying out step (i) with a silylated sulfonating agent.

More particularly the reaction scheme of the process of this invention is as follows:

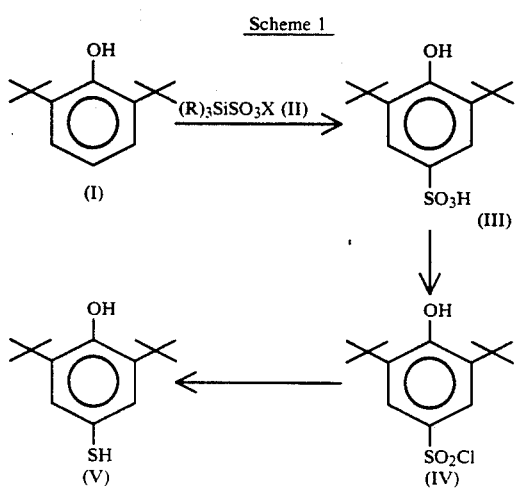

Scheme 1 wherein R is $C_1$–$C_4$ alkyl and X is Cl or Br.

The regioselective sulfonation of 2,6-di-t-butyl-phenol (I) in 4-position with silylated sulfonating agent of the formula (II) is preferably performed in an inert solvent at a temperature lower than 15° C. The most preferred range of temperature is of from $-10°$ to 15° C.

Silylated sulfonating agents of the formula (II) and methods for the preparation thereof from the corresponding chlorosilyl derivatives are known (e.g., Duffat et al., Bull. Chem. Soc. Fr., 1963, 512–5179 and Voronkov et al., Synthesis, 1982, 277–280).

The silylated sulfonating agent (II) may also be prepared "in situ". In this case it will be preferred to employ the same solvent as in the sulfonation step.

Examples of suitable sulfonating agents are trimethylsilylchlorosulfonate, trimethylsilylbromosulfonate and triethylsilylchlorosulfonate.

Most preferably, it is used trimethylsilylchlorosulfonate.

All the steps of the process of this invention are advantageously performed in the very same solvent.

Examples of suitable solvents are the aliphatic halogenated and nitro compounds having from 1 to 3 carbon atoms.

Examples of preferred solvents are methylene chloride, dichloroethane, tetrachloroethane, trichlorofluoromethane and nitromethane.

Most preferably, it is used methylene chloride.

The sulfonation step affords the acid of the formula (III) together with silyl derivatives thereof.

If desired, pure sulfonic acid (III) can be obtained by treating the sulfonation reaction mixture with water.

However, the reaction mixture containing the sulfonic acid of formula (III) and some silyl derivatives thereof is preferably treated as such with a suitable chlorinating agent to give the 2,6-di-butyl-4-hydroxybenzene-sulfonic acid chloride of the formula (IV).

Preferably, the chlorinating agent is selected from the group comprising thionyl chloride, phosphorus pentachloride, phosphorus trichloride and phosphoryl chloride.

The chlorination step may be performed in the presence of a catalytic amount (5–10%) of dimethylformamide.

The reduction of the sulfonyl chloride compound of the formula (IV) is carried out according to conventional techniques.

By way of an example, a method that gives excellent results at a low cost consists in carrying out the reaction with metal zinc in acid medium.

Alternatively, the reduction step may be carried out directly on the intermediate of formula (III) according to known techniques (J. March, Advanced Organic Chemistry, 3rd ed. page 1107, paragraph 9–54).

The thus obtained reaction mixture containing 2,6-di-t-butyl-4-mercapto-phenol (V) can be reacted with acetone to give probucol as disclosed in the mentioned British Patent No. 1199871, thus providing a one-pot process from 2,6-di-t-butyl-phenol.

A preferred embodiment of the process of this invention comprises preparing trimethylsilylchlorosulfonate (II, R=CH$_3$, X=Cl) in methylene chloride by reacting chlorosulfonic acid with trimethylsilylchloride.

The thus obtained reaction mixture is then dropped into a solution of 2,6-di-t-butylphenol (I) in methylene chloride kept at 0° C. Alternatively, a solution of 2,6-di-t-butyl-phenol in methylene chloride is added dropwise to the above-mentioned reaction mixture containing trimethylsilylchlorosulfonate maintained at a temperature of from −10° C. to 15° C.

When the addition is over, the reaction mixture is allowed to warm to room temperature and thionyl chloride and some catalytic amount of dimethylformamide are added.

After having been refluxed for some hours the reaction mixture is cooled.

In an inert atmosphere, zinc is added to the mixture and then concentrated hydrochloric acid is dropped therein.

After usual work up of the reaction mixture, 2,6-di-t-butyl-4-mercapto-phenol (V) is obtained in almost quantitative yield.

The process of this invention is very convenient on industrial scale because it implies the use of cheap reactants and can be performed in one reaction vessel with high productivity. Furthermore, it affords almost quantitative yields meanwhile avoiding formation of highly toxic or difficult to be separated by-products.

Moreover, 2,6-di-t-butyl-4-mercapto-phenol prepared according the process of this invention is highly pure and can be used in the preparation of probucol without undergoing any further purification.

A further noteworthy advantage is that probucol prepared from crude 2,6-di-t-butyl-4-mercapto-phenol of this invention meets, after a simply crystallization, with the chemical-physical specification of USP XXII, page 1143.

Highly pure 2,6-di-t-butyl-4-mercapto-phenol is also useful as intermediate for preparing further drugs like, for example, the compounds described in EP-A-0 235 575 (Searle Co.), EP-A-O 348 203 (Shionigi & Co.), DE-A-2 406 812 (Dow Chemical Co.) and JP-A-62-81343 (Otsuka Pharmaceutical Inc.).

The following examples are given to better illustrate this invention without, however, limiting it in any way.

EXAMPLE 1

Preparation of 2,6-t-butyl-4-hydroxy-benzene-sulfonic acid

Methylene chloride (135 g) and trimethylsilylchloride (10.8 g; 0.1 moles) were placed, under nitrogen atmosphere, in a 500 ml double jacket vessel equipped with condenser, thermometer and mechanical stirrer. The mixture was heated to reflux (40° C.) and chlorosulfonic acid (11.3 g; 0.097 moles) was added dropwise over 10 minutes.

The mixture was refluxed for one hour. The solution was cooled to 15° C. and a solution of 2,6-di-t-butyl-phenol (20 g; 0.097 moles) in methylene chloride (15 g) was added dropwise over 20 minutes.

The thus obtained solution was used in the next reaction step without undergoing any further treatment.

A small sample of the reaction mixture was treated with water and the solution was evaporated under vacuum to give a product which, after crystallization from benzene, proved to be pure 2,6-di-t-butyl-4-hydroxy-benzenesulfonic acid.

$^1$H-NMR (300 MHz, CDCl$_3$), delta (ppm): 1.43 (s, 18H); 6.45 (broad signal, —SO$_3$H and /or —OH); 7.7 (s, 2H). $^{13}$C-NMR (74.5 MHz, CDCl$_3$) delta (ppm); q 29.97; s 34.52; d 123.89; s 129.78; s 136.46; d 157.64.

m.p.=142°–144° C.

EXAMPLE 2

Preparation of 2,6-di-t-butyl-4-hydroxy-benzene-sulfonic acid chloride

To the methylene chloride solution of example 1, kept at room temperature, dimethylformamide (0.7 g, 0.0097 moles) and then thionyl chloride (13.8 g; 0.116 moles) were added.

The mixture was warmed to reflux and refluxed for 18 hours.

The thus obtained solution was used in the next reaction step without undergoing any further treatment.

A small sample of this solution gave, after evaporation of the solvent under vacuum, the desired product.

$^1$H-NMR (300 MHz, CDCl$_3$) delta (ppm): 1.48 (s, 18H); 6.15 (s, 1H, —OH); 7.85 (s, 2H, aromatics).

EXAMPLE 3

Preparation of 2,6-di-t-butyl-4-mercapto-phenol

The methylene chloride solution of example 2, containing 2,6-di-t-butyl-4-hydroxybenzenesulfonic acid chloride, was made inert with nitrogen gas and cooled to 15° C. Zinc powder (44.6 g; 0.068 moles) was added portionwise and then 37% aqueous hydrochloric acid (188 g; 1.9 moles) was added dropwise over 2 hours under vigorous stirring.

When the addition was over, the reaction mixture was brought to room temperature and maintained under stirring for 3 hours.

The reaction mixture was filtered under nitrogen gas, the phases were separated, the aqueous phase was extracted with methylene chloride (30 g). The combined organic phases were washed with deionized water (2×30 g) and finally with a saturate solution of sodium chloride (30 g).

The thus obtained organic solution was evaporated under vacuum at 25° C. A solid was obtained (21.85 g; overall yield, 94.6% with respect to 2,6-di-t-butyl-phenol of the example 1) consisting of 2,6-di-t-butyl-4- mercapto-phenol which was used in the next reaction step without undergoing any further treatment.

A small sample was analyzed after removal of the solvent under vacuum and crystallization from pentane. m.p.=68° C.

$^1$H-NMR (300 MHz, CDCl$_3$) delta (ppm): 1.42 (s, 18H); 3.38 (s, 1H), —SH); 5.16 (s, 1H, —OH); 7.17 (s, 2H, aromatics).

EXAMPLE 4

Preparation of 4,4'-(isopropylidenedithio)-bis-[2,6-di-t-butyl-phenol]

In a 100 ml double jacket vessel equipped with mechanical stirrer, thermometer and condenser, crude 2,6-di-t-butyl-4-mercapto-phenol (21.85 g; 0.0916 moles), prepared as described in example 3, and methyl alcohol (30 g) were placed under nitrogen gas.

The mixture was stirred until solubilization and then 37% aqueous hydrochloric acid (0.5 g) and thereafter acetone (5.27 g) were added dropwise.

The solution was refluxed (65° C.) for 4 hours and then cooled to room temperature.

A suspension was thus obtained that was cooled to 0° C.

The mixture was filtered, and the solid was washed with methyl alcohol (2×5 g) at 0° C. and dried under vacuum at 60° C.

A crude product (18.9 g) was thus obtained which was crystallized twice from a mixture of isopropyl alcohol and water (95:5).

4,4'-(isopropylindenedithio)-bis-[2,6-di-t-butyl-phenol] (probucol) was obtained after filtering and drying under vacuum at 60° C. (17 g; overall yield; 66.6% with respect to 2,6-di-t-butylphenol of example 1).

$^1$H-NMR (300 MHz, CDCl$_3$) delta (ppm): 1.45 (s, 42H); 5.37 (s, 2H, —OH); 7.47 (s, 4H, aromatics).

EXAMPLE 5

Preparation of 2,6-di-t-butyl-4-hydroxybenzenesulfonic acid

Methylene chloride (337.5 g) and 98% trimethylsilylchloride (29.8 g; 0.2675 moles) were placed, under nitrogen atmosphere, in a 1000 ml vessel equipped with condenser, thermometer and mechanical stirrer. The mixture was heated to reflux (40° C.) and 98% chlorosulfonic acid (28.82 g; 0.2425 moles) was added dropwise over 10 minutes.

The mixture was refluxed for one hour. The reaction mixture was cooled to 0° C. and added dropwise to a solution of 2,6-di-t-butyl-phenol (50 g; 0.2425 moles) in methylene chloride (37.5 g) over 30 minutes at 0°-5° C.

The thus obtained solution was used in the preparation of 2,6-di-t-butyl-4-hydroxy-benzene-sulfonic acid chloride (Example 2) and then of 2,6-di-t-butyl-4-mercapto-phenol (Example 3). The yield of 2,6-di-t-butyl-4-mercapto-phenol with respect to 2,6-di-t-butyl-phenol was of 95%.

We claim:

1. In a process for preparing 2,6-di-t-butyl-4-mercapto-phenol comprising (i) the sulfonation of 2,6-di-t-butyl-phenol, (ii) the optional preparation of a reducible derivative of the thus obtained 2,6-di-t-butyl-4-hydroxybenzenesulfonic acid, and (iii) the reduction of the 2,6-di-t-butyl-4-hydroxy-benzenesulfonic acid or of a reducible derivative thereof, the improvement comprising carrying out step (i) with a silylated sulfonating agent of formula (II) (R)$_3$SiSO$_3$X wherein R is C$_1$–C$_4$ alkyl and X is Cl or Br.

2. A process according to claim 1, wherein the silylated sulfonating agent is selected from the group consisting of trimethylsilylchlorosulfonate, trimethylsilylbromosulfonate and triethylsilylchlorosulfonate.

3. A process according to claim 2, wherein the silylated sulfonating agent is trimethylsilylchlorosulfonate.

4. A process according to claim 1, wherein step (i) is performed at a temperature of from −10° C. to 15° C.

5. A process according to claim 1, wherein steps (i), (ii) and (iii) are performed in the same solvent without separating any intermediate product.

6. A process according to claim 5, wherein the solvent is an aliphatic halogenated or nitro compound having from 1 to 3 carbon atoms.

7. A process according to claim 6, wherein the solvent is methylene chloride, dichloroethane, tetrachloroethane, trichlorofluoromethane or nitromethane.

* * * * *